US010111784B2

(12) United States Patent
Wada

(10) Patent No.: US 10,111,784 B2
(45) Date of Patent: Oct. 30, 2018

(54) DEVICE FOR PRODUCING DISPOSABLE WEARABLE ARTICLE AND METHOD FOR PRODUCING DISPOSABLE WEARABLE ARTICLE

(71) Applicant: ZUIKO CORPORATION, Settsu-shi, Osaka (JP)

(72) Inventor: Takao Wada, Osaka (JP)

(73) Assignee: Zuiko Corporation, Settsu-shi, Osaka (JP)

( * ) Notice: Subject to any disclaimer, the term of this patent is extended or adjusted under 35 U.S.C. 154(b) by 352 days.

(21) Appl. No.: 15/023,828

(22) PCT Filed: Sep. 25, 2014

(86) PCT No.: PCT/JP2014/075347
§ 371 (c)(1),
(2) Date: Mar. 22, 2016

(87) PCT Pub. No.: WO2015/046283
PCT Pub. Date: Apr. 2, 2015

(65) Prior Publication Data
US 2016/0235593 A1    Aug. 18, 2016

(30) Foreign Application Priority Data

Sep. 30, 2013    (JP) ................................. 2013-204614
Sep. 30, 2013    (JP) ................................. 2013-204615
Sep. 30, 2013    (JP) ................................. 2013-204616

(51) Int. Cl.
*A61F 13/15*        (2006.01)
*B29C 65/00*        (2006.01)
(Continued)

(52) U.S. Cl.
CPC .. *A61F 13/15747* (2013.01); *A61F 13/15585* (2013.01); *A61F 13/15739* (2013.01);
(Continued)

(58) Field of Classification Search
CPC .......... A61F 13/15747; A61F 13/15764; A61F 13/15739; A61F 13/15585;
(Continued)

(56) References Cited

U.S. PATENT DOCUMENTS 4,816,100 A * 3/1989 Friese ................... A61F 13/206
                                                156/191
6,546,987 B1 * 4/2003 Tachibana ............... B29C 65/18
                                                156/555
(Continued)

FOREIGN PATENT DOCUMENTS

CN        1184449 A      6/1998
CN        1386481 A     12/2002
(Continued)

OTHER PUBLICATIONS

Chinese Office Action Application No. 201320618286.2 dated May 27, 2016.
(Continued)

*Primary Examiner* — Carson Gross
*Assistant Examiner* — Christian Roldan
(74) *Attorney, Agent, or Firm* — Gerald E. Hespos; Michael J. Porco; Matthew T. Hespos

(57) ABSTRACT

A joining/cutting unit (60) includes a drum (61) having a peripheral surface (61*a*) on which a sheet (W) is to be placed, joining mechanisms (601 to 603), a cutting mechanism (604) arranged downstream of the joining mechanism (603) in a rotating direction of the drum (61), claw members (607) vertically movably mounted on the peripheral surface (61*a*) of the drum (61) and a vertically moving cam mechanism (630) configured to vertically move the claw members (607). The vertically moving cam mechanism (630) includes a cam disc (635) having an eccentric cam groove (634) and cam followers (633) configured to be engaged with the
(Continued)

eccentric cam groove (634) so that the claw members (607) vertically move according to the rotation of the drum (61). Further, the joining/cutting unit (60) further includes a phase adjusting mechanism (631) provided on the cam disc (635) and capable of adjusting a phase of the eccentric cam groove (634).

8 Claims, 8 Drawing Sheets

(51) Int. Cl.
| | | |
|---|---|---|
| *B29C 65/78* | (2006.01) | |
| *B29C 65/18* | (2006.01) | |
| *B29L 31/48* | (2006.01) | |

(52) U.S. Cl.
CPC ........ *A61F 13/15764* (2013.01); *B29C 65/18* (2013.01); *B29C 65/7847* (2013.01); *B29C 65/7882* (2013.01); *B29C 66/0326* (2013.01); *B29C 66/1122* (2013.01); *B29C 66/431* (2013.01); *B29C 66/433* (2013.01); *B29C 66/81465* (2013.01); *B29C 66/82263* (2013.01); *B29C 66/82265* (2013.01); *B29C 66/83513* (2013.01); *A61F 2013/15861* (2013.01); *B29L 2031/4878* (2013.01)

(58) Field of Classification Search
CPC ..... A61F 2013/15861; B29C 66/82265; B29C 66/82263; B29C 65/18; B29C 66/81465; B29C 66/431; B29C 66/1122; B29C 66/0326; B29C 66/83513; B29C 65/7847; B29C 66/433; B29C 65/7882; B29L 2031/4878
USPC .......................................................... 156/250
See application file for complete search history.

(56) References Cited

U.S. PATENT DOCUMENTS

| | | | |
|---|---|---|---|
| 7,846,082 B2* | 12/2010 | Burns, Jr. ......... | A61F 13/15747 493/424 |
| 8,096,931 B2* | 1/2012 | Yamamoto ........ | A61F 13/15699 493/343 |
| 9,168,183 B2* | 10/2015 | Yamamoto ........ | A61F 13/15747 |
| 2002/0174930 A1 | 11/2002 | Umebayashi | |
| 2003/0047273 A1* | 3/2003 | Kojo ................ | A61F 13/15609 156/250 |
| 2005/0125981 A1* | 6/2005 | Yamamoto ........ | A61F 13/15747 29/426.6 |
| 2008/0006989 A1* | 1/2008 | Masaki .................. | B65H 9/06 271/202 |
| 2010/0122766 A1 | 5/2010 | Yamamoto | |
| 2012/0090774 A1* | 4/2012 | Ogasawara ....... | A61F 13/15756 156/196 |

FOREIGN PATENT DOCUMENTS

| | | |
|---|---|---|
| CN | 101096247 A | 1/2008 |
| CN | 102078242 A | 6/2011 |
| CN | 102215800 A | 10/2011 |
| CN | 102256578 A | 11/2011 |
| EP | 1552799 A1 | 7/2005 |
| JP | 2000-255518 | 9/2000 |
| JP | 2003-038566 | 2/2003 |
| JP | 3910478 | 2/2007 |
| JP | 2007-260414 | 10/2007 |
| JP | 4359357 | 8/2009 |
| JP | 5089821 | 12/2012 |
| JP | 2013-126528 | 6/2013 |
| WO | 9636487 A1 | 11/1996 |

OTHER PUBLICATIONS

Chinese Office Action Application No. 201320617874.2 dated May 27, 2016.
European Search Report dated Sep. 1, 2016.
International Search Report.

* cited by examiner

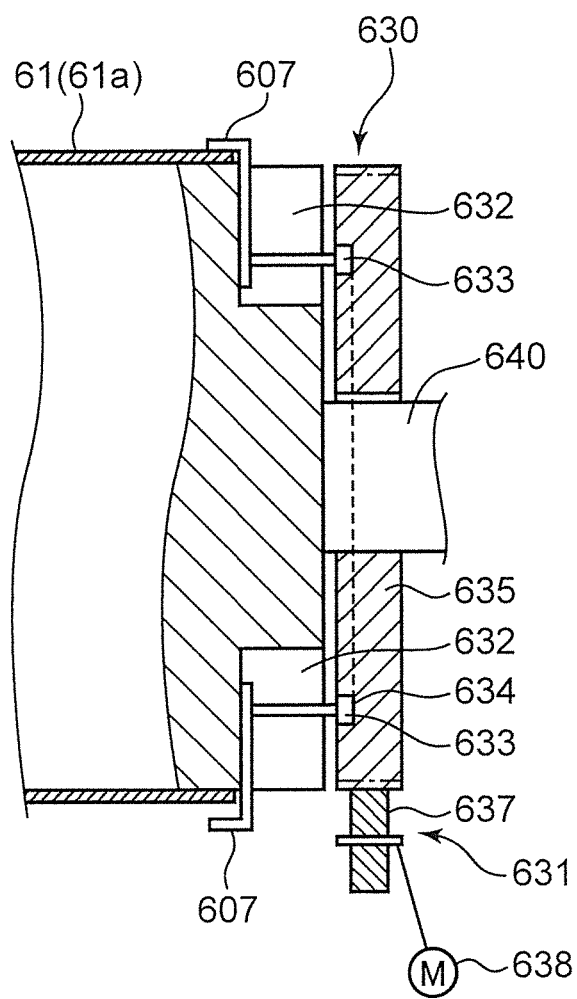

DEVICE FOR PRODUCING DISPOSABLE WEARABLE ARTICLE AND METHOD FOR PRODUCING DISPOSABLE WEARABLE ARTICLE

TECHNICAL FIELD

The present invention relates to a device and a method for producing a disposable wearable article.

BACKGROUND ART

Conventionally, a device provided with an absorber arranging unit 10, an elastic attaching unit 20, a hole forming unit 30 and a doubling unit 40, a twisting unit 50 and a joining/cutting unit 60 in a line for continuously conveying a sheet W in a horizontal direction (direction to make a sheet width direction horizontal) as shown in FIG. 7 is known as a device for producing a disposable wearable article (see Publication of Japanese Patent No. 3910478).

In the absorber arranging unit 10, absorbers C are arranged at a predetermined interval on a surface of the sheet W from a drum 11. In the elastic attaching unit 20, at least one(s) of a waist elastic F and leg elastics for leg gather is/are attached to the surface of the sheet W. In the hole forming unit 30, holes H, which will serve as leg holes, are perforated at opposite sides of the absorber C in a conveying direction of the sheet W. In this way, a part of the sheet W having the absorber C arranged thereon functions as a crotch part.

In the doubling unit 40, the sheet W is doubled together with the absorber C in a vertical direction (direction perpendicular to the sheet width direction) by a doubling member 41 such that opposite side edges W1, W2 of the sheet W are proximate to or overlapped with each other.

In the twisting unit 50, the doubled sheet is returned to a horizontal orientation by being twisted 90° while being guided using a plurality of guiding bars 51.

In the joining/cutting unit 60, after parts of the doubled sheet W at the opposite sides of the absorber C (opposite sides of a waist part) are joined on a drum 61, these joined parts are cut. In this way, a pants-type disposable wearable article P is separated from the sheet W. Note that, in FIG. 7, the posture of the separated disposable wearable article P is turned 90° on the line.

In the device for producing a disposable wearable article as described above, after parts at opposite sides of the crotch part of the doubled sheet are joined on the drum 61, these joined parts are cut in the cutting/joining unit.

Here, there is also a device including a claw member for pressing the parts of the doubled sheet W at the opposite sides of the crotch part against the peripheral surface of the drum on a side upstream of a joining position in the conveying direction of the sheet W so that the joining position and a cutting position of the sheet W are not shifted (see Publication of Japanese Patent No. 4359357).

This device includes a drive cam mechanism for periodically moving the claw member according to the rotation of the drum. The drive cam mechanism is provided with a cam disc disposed to face a side surface of the drum, and the cam disc includes an eccentric cam groove to be engaged with a cam follower of the claw member and is fixed to an installation surface of the device.

However, a timing at which the claw member presses the parts of the doubled sheet at the opposite sides of the crotch part against the peripheral surface of the drum differs, for example, depending on the size of a wearable article (L size, M size, S size, etc.). Here, since being fixed to the installation surface of the device, the cam disc has to be replaced with the one having an eccentric cam groove in conformity with the size of wearable articles to change the size of the wearable articles to be produced, thereby causing problems such as a reduction in the production efficiency of wearable articles.

SUMMARY OF INVENTION

The present invention aims to provide a device and a method for producing a disposable wearable article capable of improving the production efficiency of wearable articles by adjusting a sheet pressing timing of a claw member without exchanging a cam disc.

To solve the above problem, the present invention provides a device for producing a disposable wearable article, the device including a doubling unit provided in a line for continuously conveying a sheet and configured to double the sheet together with an absorber such that opposite side edges of the sheet having the absorber arranged thereon are proximate to or overlapped with each other, and a joining/cutting unit provided in the line and configured to join parts of the doubled sheet at opposite sides of a crotch part having the absorber arranged thereon and then cut the joined parts, the joining/cutting unit including a drum having a peripheral surface and rotatable with the doubled sheet placed on the peripheral surface, at least one joining mechanism configured to join the parts of the doubled sheet at the opposite sides of the crotch part between the joining mechanism and the drum, a cutting mechanism arranged downstream of the joining mechanism in a rotating direction of the drum and configured to cut the parts of the sheet joined by the joining mechanism between the cutting mechanism and the drum, a claw member mounted on the drum to be vertically movable with respect to the peripheral surface of the drum, and a vertically moving cam mechanism configured to move the claw member downward to press a part of the sheet between the crotch parts against the peripheral surface of the drum on a side upstream of the joining mechanism in the rotating direction of the drum and move the claw member upward to release the pressing on a side downstream of the cutting mechanism in the rotating direction of the drum, the vertically moving cam mechanism including a cam disc having an eccentric cam groove, facing a side surface of the drum and coaxially arranged with the drum and a cam follower provided on the claw member and configured to be engaged with the eccentric cam groove so that the claw member vertically moves according to the rotation of the drum, and the joining/cutting unit further including a phase adjusting mechanism capable of adjusting a phase of the eccentric cam groove with respect to the drum.

Further, the present invention provides a method for producing a disposable wearable article using the above device for producing a disposable wearable article, the method including a conveying process of continuously conveying a sheet, an absorber arranging process of arranging an absorber on a surface of the sheet, a doubling process of doubling the sheet together with the absorber using the above doubling unit such that opposite side edges of the sheet having the absorber arranged thereon are proximate to or overlapped with each other, and a joining/cutting process of joining parts of the doubled sheet at opposite sides of a crotch part having the absorber arranged thereon and then cutting the joined parts using the above joining/cutting unit.

According to the present invention, it is possible to improve the production efficiency of wearable articles having different sizes by adjusting a sheet pressing time of a claw member only by the rotation of a cam disc without exchanging the cam disc.

BRIEF DESCRIPTION OF DRAWINGS

FIG. 5B is a side view in section of FIG. 5A.

DESCRIPTION OF EMBODIMENT

Hereinafter, an embodiment of the present invention is described with reference to the accompanying drawings. The following embodiment is one specific example of the present invention and not of the nature to limit the technical scope of the present invention.

Figure 7:
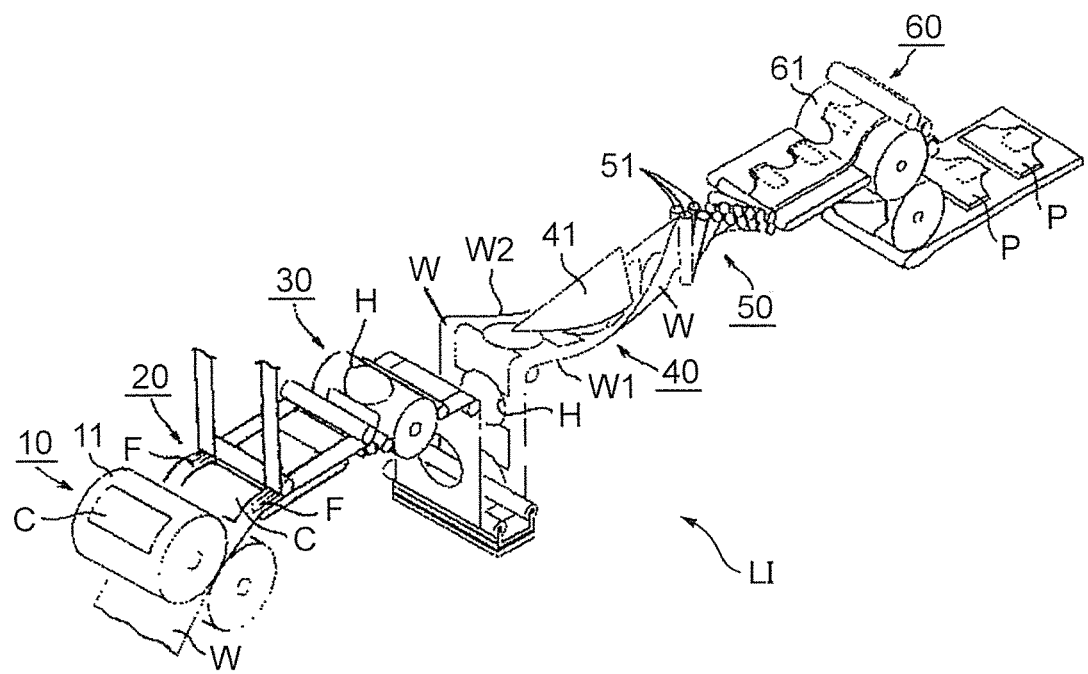
FIG. 7 is a perspective view of a device for producing a disposable wearable article according to a background art.

A device for producing a disposable wearable article according to the present invention has an overall configuration substantially similar to that of the background art of FIG. 7.

Specifically, with reference to FIG. 7, the producing device includes a line L1 for continuously conveying a sheet W in a horizontal direction (direction to make a width direction of the sheet W horizontal; the same holds true below).

Further, the device for producing a disposable wearable article includes an absorber arranging unit 10, an elastic attaching unit 20, a hole forming unit 30, a doubling unit 40, a twisting unit 50 and a joining/cutting unit 60 provided in the line L1.

The absorber arranging unit 10 intermittently arranges the absorbers C on a surface of the sheet W. The elastic attaching unit 20 attaches a waist elastic F to the surface of the sheet W. The hole forming unit 30 forms holes H, which will serve as leg holes, on the sheet W. The doubling unit 40 doubles the sheet W in a vertical direction (direction perpendicular to the width direction of the sheet W; the same holds true below) such that opposite side edges W1, W2 of the sheet W are proximate to or overlapped with each other. The twisting unit 50 returns the doubled sheet W to a horizontal orientation. The joining/cutting unit 60 joins parts at opposite sides of a part of the doubled sheet W having the absorber C arranged thereon (crotch part) and, then, cuts these joined parts.

Although the absorbers C are directly arranged on the sheet W by the drum 11 and the like in the absorber arranging unit 10 here, the absorbers C may be arranged on another sheet and, thereafter, this other sheet may be placed on the sheet W.

Although the waist elastic F is attached to the sheet W having the absorber C arranged thereon in the elastic attaching unit 20, the waist elastic F may be attached between another sheet and the sheet W. Further, if leg elastics for leg gather are attached to the sheet W before the absorber C is arranged, the waist elastic F may be attached onto the sheet W when the leg elastics are introduced.

In the hole forming unit 30, the holes H, which will become leg holes, are perforated at a predetermined interval on the sheet W having the waist elastic F attached thereto by an unillustrated leg hole cutter. Members cut out from the sheet W are discharged to the outside of a production line system by unillustrated vacuum. In this way, the part of the sheet W having the absorber C arranged thereon (part between the holes H) becomes the crotch part. Note that the holes H, which will become leg holes, may be perforated before the waist elastic F is introduced or before the absorber C is arranged.

After the holes H are perforated on the sheet W and the waist elastic F is arranged, the sheet W is introduced to the doubling unit 40. The bottom edge of a doubling member 41 of the doubling unit 40 comes into contact with a substantially center of the sheet W in the width direction, and the sheet W is doubled together with the absorber C such that the first side edge W1 and the second side edge W2 thereof are matched. The position of the doubling member 41 may be adjustable in the vertical and lateral directions.

The doubled sheet W is returned to the horizontal orientation by being twisted 90° by the twisting (twist) unit 50. Specifically, the sheet W is doubled in the vertical direction along a substantially vertical plane in the doubling unit 40. To facilitate sealing in a later process, the sheet W is returned to the horizontal orientation along a substantially horizontal plane by the twisting unit 50 and conveyed in this state.

The sheet W twisted by the twisting unit 50 is sealed on a drum 61 of the joining/cutting unit 60. The sheet W may be sealed, for example, by a heat-seal method disclosed in Publication of Japanese Patent No. 4359357 or may be sealed by ultrasonic welding. By sealing, adjacent disposable wearable articles P are partitioned from each other. The wearable articles P partitioned by sealing are cut by cutters 613 (see FIG. 1) to be separated from the sheet W.

Note that, if necessary, the posture of the wearable article P may be turned 90° and an interval between adjacent wearable articles P may be changed. For example, the wearable articles P may be placed on a pad moving above the drum and the posture of the pad may be turned 90° or the interval of the wearable articles P may be changed by changing a speed of the pad.

Figure 1:
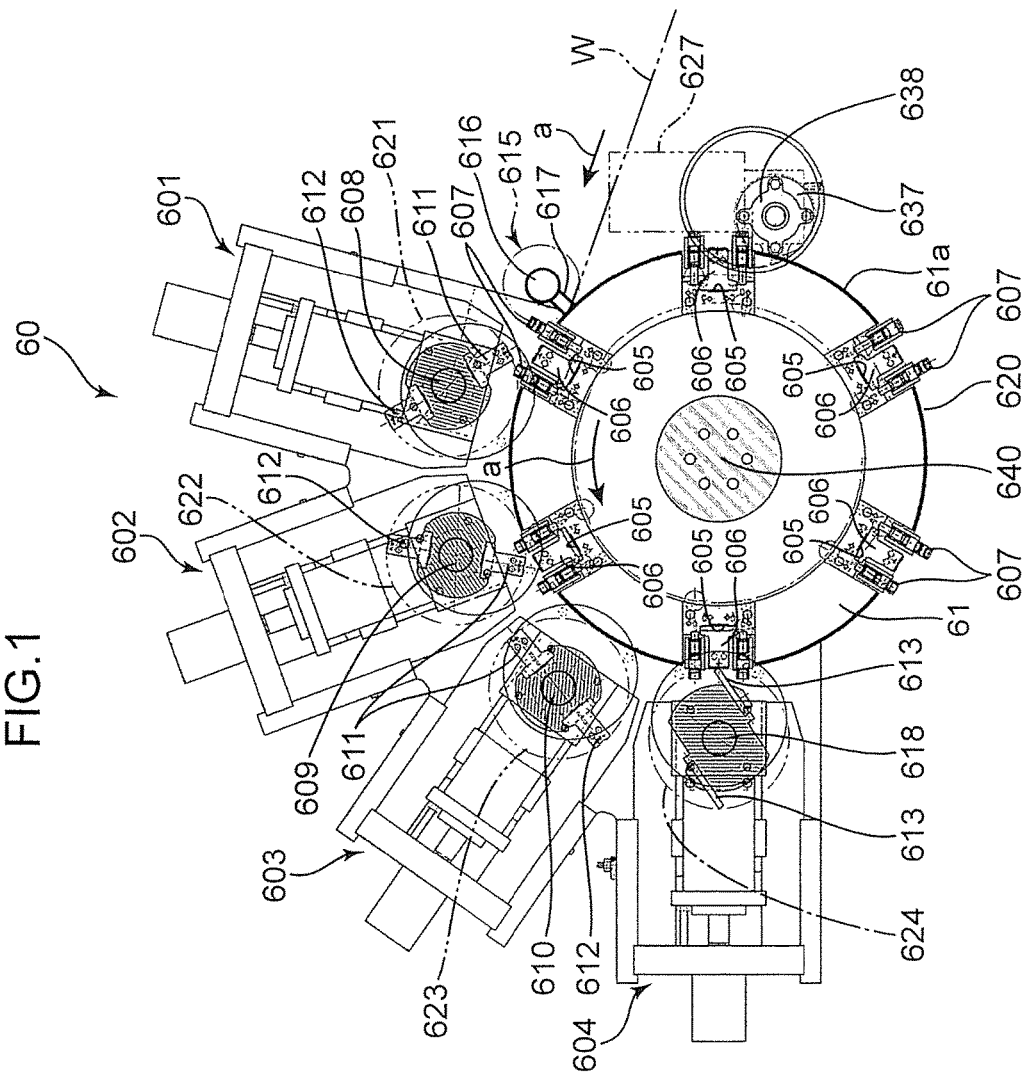
FIG. 1 is a side view of a joining/cutting unit in a device for producing a disposable wearable article according to the present invention.
Figure 2:
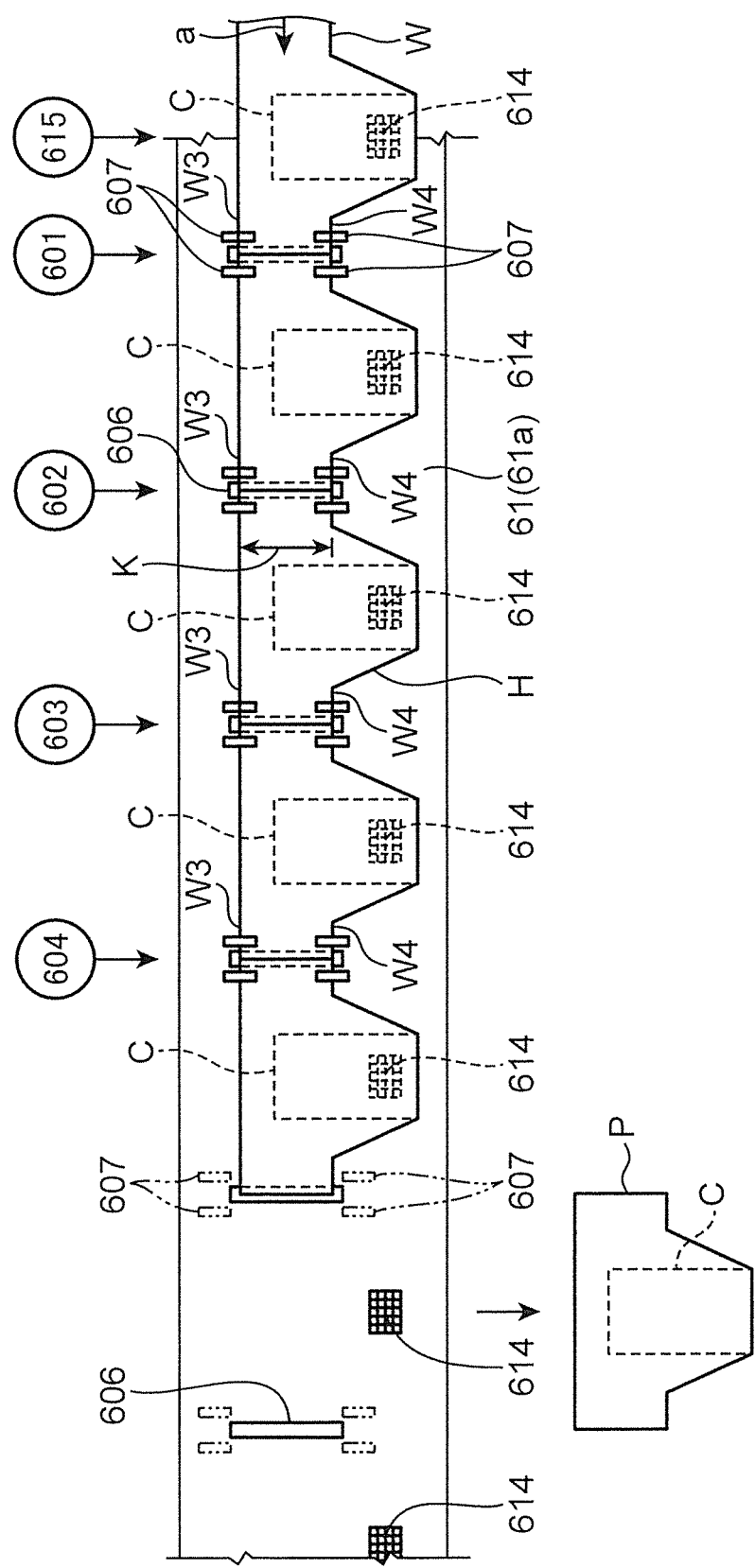
FIG. 2 is a plan view of a drum of FIG. 1 unfolded in a circumferential direction.

The specific configuration of the joining/cutting unit 60 is described below. FIG. 1 is a side view of the joining/cutting unit 60. FIG. 2 is a plan view of the drum 61 unfolded in a circumferential direction. The doubled sheet W is continuously conveyed in the horizontal orientation from right to left as indicated by a conveying direction a shown by an arrow.

The joining/cutting unit 60 includes the drum 61 that is rotated along the conveying direction a substantially at the same speed as a conveying speed of the doubled sheet W. The drum 61 has a peripheral surface 61a and is rotatable with the doubled sheet W placed on the peripheral surface 61a. That is, the lower surface of the doubled sheet W is placed on the peripheral surface 61a of the drum 61.

Further, the joining/cutting unit 60 includes first to third joining mechanism 601, 602 and 603 for successively heat-sealing the same parts of the doubled sheet W at the opposite sides of the crotch part having the absorber C arranged thereon three times between the joining mechanism 601, 602 and 603 and the drum 61 and a cutting mechanism 604 arranged downstream of the joining mechanisms 601 to 603 in a rotating direction of the drum 61. The cutting mechanism includes the cutters 613 for cutting the parts of the sheet W joined by the joining mechanisms 601 to 603 between the cutting mechanism and the drum 61.

The drum 61 is formed with recesses 605 arranged at an interval (at an interval of 60° in this example) in the circumferential direction of the drum 61 and extending an axial direction of the drum 61. The drum 61 includes anvils (joining tables) 606 mounted in the respective recesses 605 and outer surfaces of the anvils 606 are arranged on a virtual circumferential surface having a radius substantially equal to the peripheral surface 61*a* of the rum 61. As shown in FIG. 2, each anvil 606 is longer than a length K of the parts of the doubled sheet W at the opposite sides of the crotch part and extends along the axial direction of the drum 61. In this embodiment, the sheet W can be joined and cut at six positions by one rotation of the drum 61, whereby six wearable articles P can be cut out and produced.

Further, the joining/cutting unit 60 includes a plurality of claw members 607 respectively provided at the positions of the anvils 606 on the peripheral surface of the drum 61. The claw members 607 are for pressing one side edge part W3 of the doubled sheet W, which will serve as upper edge parts of the wearable articles P, and the other side edge part W4 on the side of the holes H, which will serve as leg holes, between the crotch parts against the peripheral surface 61*a* of the drum 61.

Specifically, four claw members 607 are provided in each part of the drum 61 where the anvil 606 is provided. Out of these claw members 607, two claw members 607 provided on the side of the side edge part W3 are for pressing the side edge part W3 against the peripheral surface 61*a* at opposite sides of the anvil 606 in the conveying direction a. Out of these claw members 607, two claw members 607 provided on the side of the side edge part W4 are for pressing the side edge part W4 against the peripheral surface 61*a* at the opposite sides of the anvil 606 in the conveying direction a.

Further, as shown in FIGS. 1 and 2, the joining/cutting unit 60 includes a vertically moving cam mechanism 630 for moving the claw members 607 downward (movement in a direction toward the peripheral surface 61*a* of the drum 61) to press the part of the sheet W between the crotch parts on a side upstream of the joining mechanism 601 in the rotating direction of the drum 61 and moving the claw member 607 upward (movement in a direction away from the peripheral surface 61*a* of the drum 61) to release the pressing on a side downstream of the cutting mechanism 604 in the rotating direction of the drum 61. The vertically moving cam mechanism 630 is described in detail later.

The first to third joining mechanisms 601 to 603 are arranged side by side in the rotating direction of the drum 61.

Further, each of the first to third joining mechanism 601 to 603 includes a joining rotary shaft 608 to 610 parallel to the rotary shaft of the drum 61 and a pair of seal blocks (seal member) 611, 612 mounted on the joining rotary shaft 608 to 610 to be rotatable about the joining rotary shaft 608 to 610 and configured to join the parts of the sheet W. The pair of seal blocks 611, 612 are mounted at an interval of 180° on the joining rotary shaft 608 to 610.

Each joining rotary shaft 608 to 610 is drivingly rotated in synchronization with the drum 61. Specifically, the joining rotary shaft 608 to 610 and the drum 61 are synchronized such that the sheet W is sandwiched between one of the seal blocks 611, 612 and the anvil 606 and heat-sealed when the part of the sheet W between the crotch parts comes to the position of the first to third joining mechanism 601 to 603. Further, the joining rotary shafts 608 to 610 and the drum 61 are synchronized such that the same part of the sheet W is successively heat-sealed three times by the first to third joining mechanisms 601 to 603.

The cutting mechanism 604 includes a cutting rotary shaft 618 parallel to the rotary shaft of the drum 61 and a pair of cutters 613 mounted on the cutting rotary shaft 618 to be rotatable about the cutting rotary shaft 618 and configured to cut the joined parts of the sheet W. The pair of cutters 613 are mounted at an interval of 180° on the cutting rotary shaft 618.

The cutting rotary shaft 618 is drivingly rotated in synchronization with the drum 61. Specifically, the cutting rotary shaft 618 and the drum 61 are synchronized such that the sheet W is sandwiched and cut between one cutter 613 and the anvil 606 when the heat-sealed part between the crotch parts comes to the position of the cutting mechanism 604.

Further, the joining/cutting unit 60 includes a synchronously rotating mechanism 639 for rotating each joining rotary shaft 608 to 610, the cutting rotary shaft 618 and a pressing rotary shaft 616 to be described later in synchronization with the drum 61. The configuration of the synchronously rotating mechanism 639 is described in detail later.

As shown in FIG. 2, the peripheral surface 61*a* of the drum 61 is formed with a multitude of air suction holes 614 for sucking and holding the crotch part of the sheet W at a substantially middle position between adjacent anvils 606 in the circumferential direction of the drum 61.

The joining/cutting unit 60 further includes a pressing mechanism 615 provided on a carry-in side of the doubled sheet W to the drum 61, i.e. at a position immediately before the first joining mechanism 601 in the conveying direction a. The pressing mechanism 615 presses the crotch part against the air suction holes 614 of the peripheral surface 61*a* of the drum 61 when the doubled sheet W is carried in to the peripheral surface 61*a* of the drum 61.

Figure 3A:
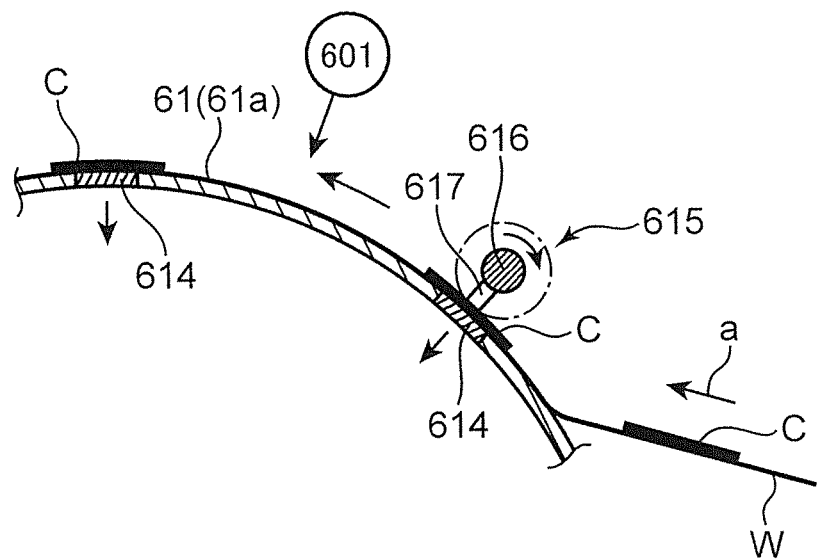
FIG. 3A is a side view of a pressing mechanism of FIG. 1.
Figure 3B:
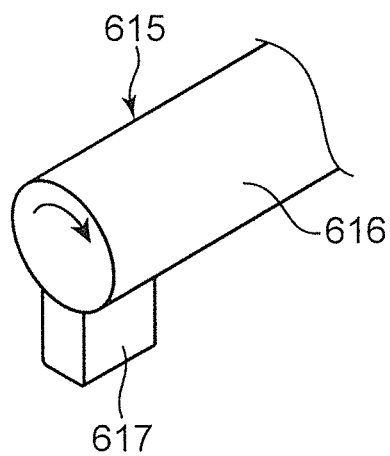
FIG. 3B is a perspective view of a pressing rotary shaft and a pressing cam of the pressing mechanism of FIG. 1.

As shown in FIGS. 3A and 3B, this pressing mechanism 615 includes the pressing rotary shaft (rotational shaft) 616 to be synchronously rotated with the drum 61 and parallel to the axial direction of the drum 61 and a pressing cam 617 projecting radially outwardly of the pressing rotary shaft 616 from the pressing rotary shaft 616 and configured to press the crotch part of the sheet W against the air suction holes 614 of the peripheral surface 61*a* of the drum 61 in a pinpoint manner.

According to the pressing mechanism 615, the crotch part can be pressed against the air suction holes 614 of the peripheral surface 61*a* of the drum 61 when the doubled sheet W is carried in to the peripheral surface 61*a* of the drum 61. This enables the crotch part to be carried in to the peripheral surface 61*a* of the drum 61 in a proper posture along the peripheral surface 61*a* of the drum 61.

Further, since the sheet W can be sucked and held on the peripheral surface 61*a* of the drum 61 by sucking air through the air suction holes 614, the lift of the crotch part can be prevented by holding the crotch part on the peripheral surface 61*a* of the drum 61 against an inertial force associated with the rotation of the drum 61.

As a result, the part of the sheet W between the crotch parts is held at a proper position on the peripheral surface of the drum 61 and joined and cut at a desired position and, on the other hand, the interference of the crotch parts with the succeeding respective joining mechanisms 601 to 603 and cutting mechanism 604 is suppressed, thereby being able to prevent the damage of the crotch parts and the like.

Further, since the crotch parts can be continuously sucked and held also after the wearable articles P are separated from the sheet W by the cutting mechanism 604, the wearable articles P can be reliably fed to the next process by releasing the suction holding at a suitable rotational position of the drum 61.

Further, the pressing cam 617 is provided on the pressing rotary shaft 616 that rotates in synchronization with the drum 61. Thus, by matching a timing at which the pressing cam 617 and the peripheral surface 61a of the drum 61 approach each other with a conveying timing of the crotch part, the crotch part can be pressed against the air suction holes 614 of the peripheral surface 61a of the drum 61 in a pinpoint manner. Therefore, the crotch part can be reliably pressed against the peripheral surface 61a while adopting a simple structure.

Figure 4:
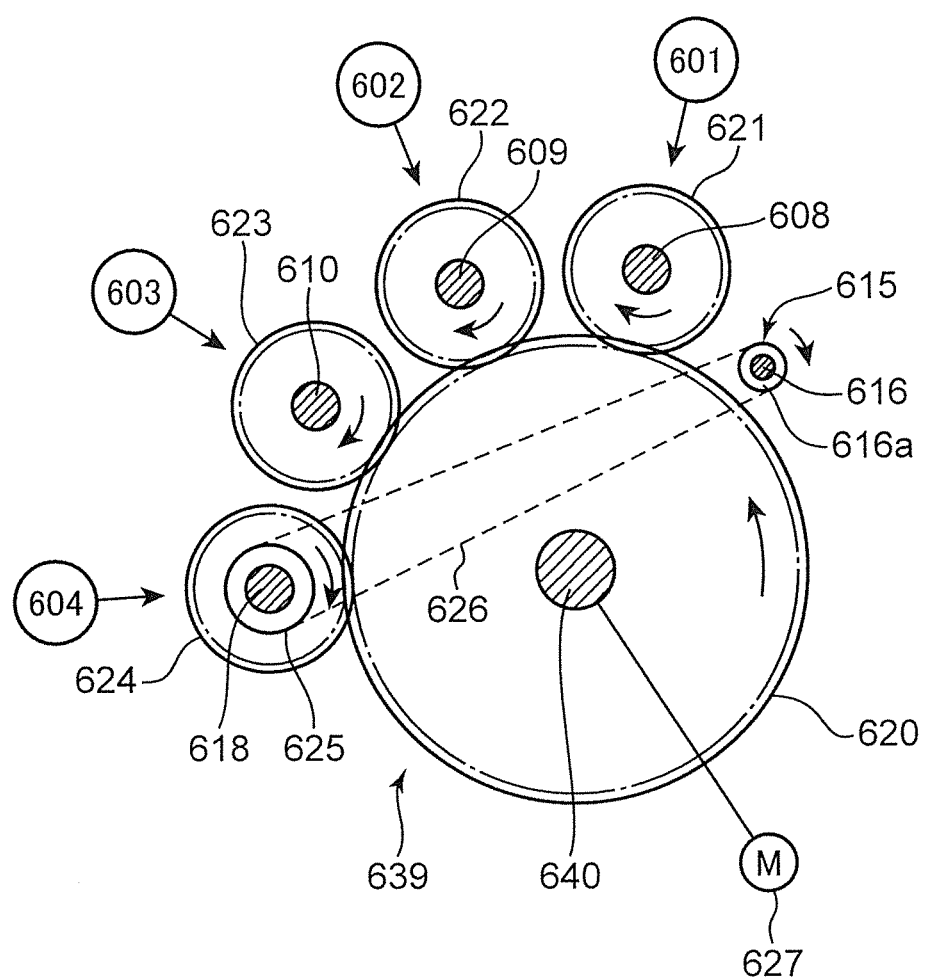
FIG. 4 is a front view diagrammatically showing a synchronously rotating mechanism for the drum, joining rotary shafts and a cutting rotary shaft.

Next, the synchronously rotating mechanism 639 for rotating the respective joining rotary shafts 608 to 610, the cutting rotary shaft 618 and the pressing rotary shaft 616 in synchronization with the drum 61 is described. FIG. 4 is a schematic front view of the synchronously rotating mechanism 639.

The synchronously rotating mechanism 639 includes a drum gear 620 having a large diameter, joining gears 621 to 623 having a small diameter and a cutting gear 624 having a small diameter.

The drum gear 620 is provided on a central rotary shaft 640 of the drum 61. Further, the joining gears 621 to 623 are respectively provided on the joining rotary shafts 608 to 610 of the joining mechanisms 601 to 603. Furthermore, the cutting gear 624 is provided on the cutting rotary shaft 618 of the cutting mechanism 604. The central rotary shaft 640 of the drum 61 is rotated by an electric motor 627.

The respective joining gears 621 to 623 and the cutting gear 624 having a small diameter are respectively directly meshed with the drum gear 620 having a large diameter.

Further, the synchronously rotating mechanism 639 includes a pulley 616a provided on the pressing rotary shaft 616 of the pressing mechanism 615, a pulley 625 provided on the cutting rotary shaft 618 of the cutting mechanism 604 and a belt 626 mounted on the both pulleys 616a, 625. In this way, the pressing mechanism 615 is rotated in synchronization with the drum 61.

According to the synchronously rotating mechanism 639, the joining gears 621 to 623 on the joining rotary shafts 608 to 610 of the joining mechanisms 601 to 603 are respectively directly meshed with the drum gear 620 of the drum 61. Further, the cutting gear 624 on the cutting rotary shaft 618 of the cutting mechanism 604 is directly meshed with the drum gear 620. The joining mechanisms 601 to 603 and the cutting mechanism 604 are driven in synchronization with the drum 61 by these meshes.

Note that, in the case of using a belt for synchronizing the joining rotary shafts 608 to 610 and the cutting rotary shaft 618 with the drum 61, there will be operational shifts between the joining rotary shafts 608 to 610, the cutting rotary shaft 618 and the drum 61 if the belt slips or is stretched. As a result, the joining positions and the cutting positions of the sheet W may vary.

In contrast, in this embodiment, the seal blocks 611, 612 and the cutters 613 can be rotated perfectly synchronized with the rotation of the drum 61 by respectively directly meshing the joining gears 621 to 623 and the cutting gear 624 with the drum gear 620. Thus, variations of the joining positions and the cutting positions of the sheet W can be prevented, with the result that the quality of wearable articles can be improved.

Note that, in this embodiment, a plurality of (three in this example) respective joining mechanisms 601 to 603 are arranged side by side in the rotating direction of the drum 61 and successively heat-seal the same part of the sheet W a plurality of times (three times in this example).

Even in the case of successively heat-sealing three times in this way, a trouble of varying three joining positions of the sheet W can be suppressed. As a result, the quality of wearable articles can be improved by reliably joining the parts of the sheet W by heat-sealing the same part a plurality of times.

Figure 5A:
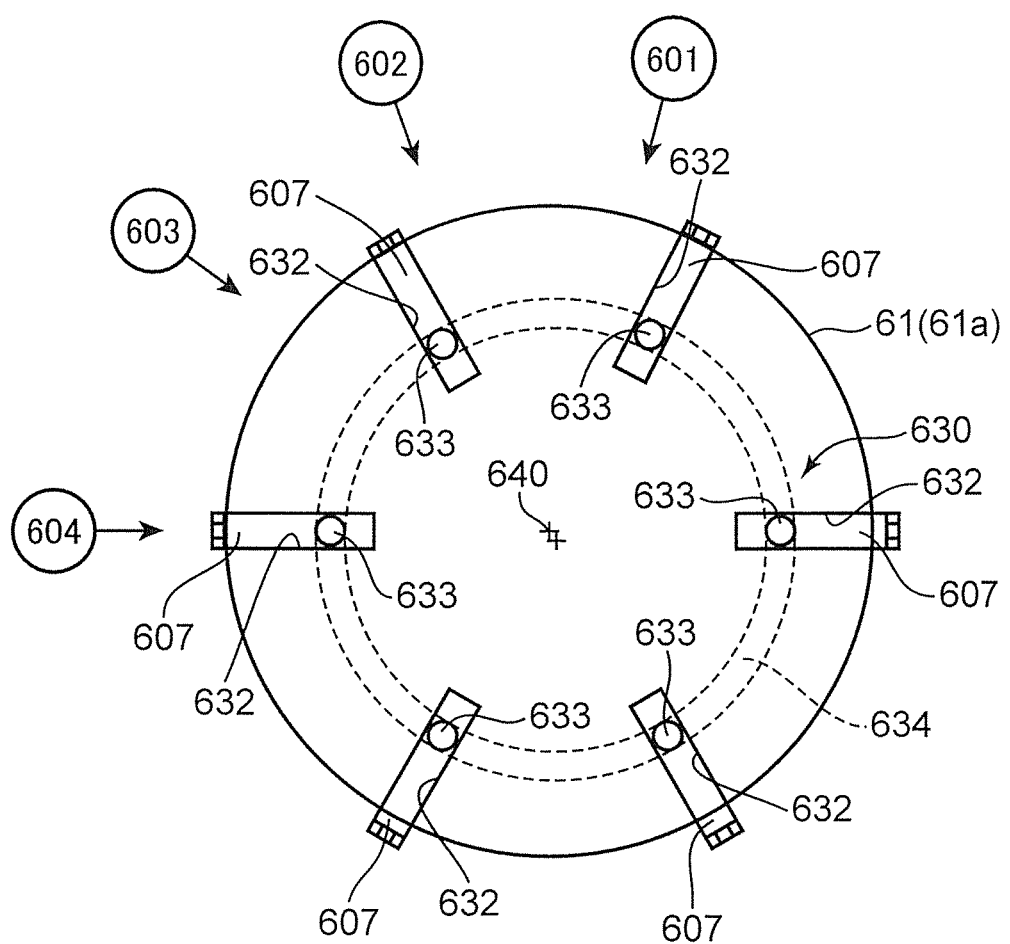
FIG. 5A is a front view diagrammatically showing a vertically moving cam mechanism for claw members.
Figure 6:
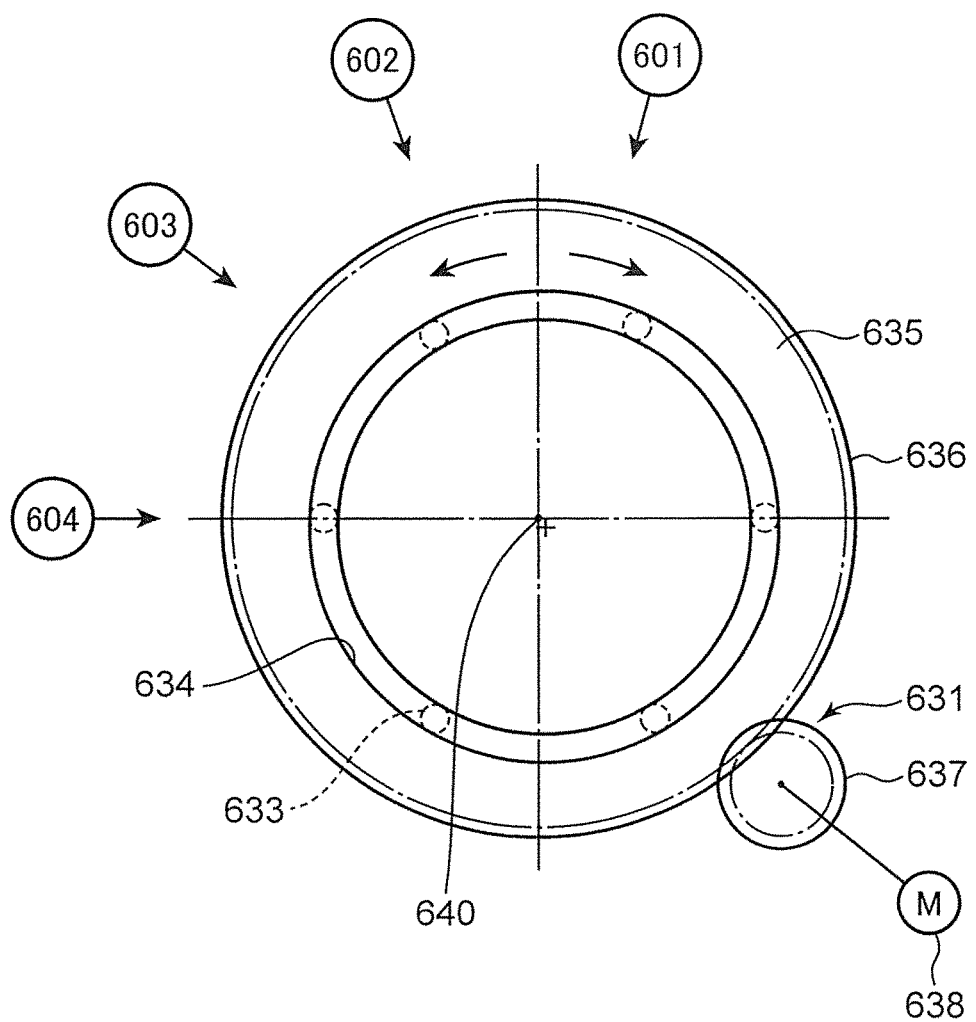
FIG. 6 is a front view diagrammatically showing a phase adjusting mechanism for the claw members.

Next, the vertically moving cam mechanism 630 and a phase adjusting mechanism 631 for the respective claw members 607 are described. FIG. 5A is a front view diagrammatically showing the vertically moving cam mechanism 630 for the claw members 607 and FIG. 5B is a side view in section of FIG. 5A. FIG. 6 is a front view diagrammatically showing the phase adjusting mechanism 631. Note that although twelve claw members 607 are shown in FIG. 1, only six claw members 607 are shown in FIG. 5A to simplify the figure.

The vertically moving cam mechanism 630 includes guide grooves 632 for vertically movably guiding the respective claw members 607, a cam disc 635 including an eccentric cam groove 634, facing a side surface of the drum 61 and coaxially arranged with the drum 61 and cam followers 633 provided on the claw member 607 and engageable with the eccentric cam groove 634 so that the claw members 607 vertically move (move in a radial direction of the drum 61) according to the rotation of the drum 61.

The guide grooves 632 are formed on opposite side surfaces (only one side surface is shown in FIG. 5) in correspondence with the positions of the respective anvils 606 (see FIG. 1). The cam followers 633 project laterally from the respective claw members 607.

The cam disc 635 is mounted on a supporting frame (not shown) facing the side surface of the drum 61, rotatably about the central rotary shaft 640 of the drum 61. The eccentric cam groove 634 is arranged to be eccentric with respect to the central rotary shaft 640 of the drum 61.

The drum 61 rotates relative to the cam disc 635 with the cam follower 633 of each claw member 607 engaged with the eccentric cam groove 634 of the cam disc 635, whereby each claw member 607 vertically moves in synchronization with the rotation of the drum 61.

Further, the joining/cutting unit 60 includes the phase adjusting mechanism 631 provided on the cam disc 635 and capable of adjusting the phase of the eccentric cam groove 634 with respect to the drum 61.

The phase adjusting mechanism 631 includes a cam gear 636 formed on the outer periphery of the cam disc 635, a cam drive gear 637 meshed with the cam gear 636 and an electric motor 638 for drivingly rotating the cam drive gear 637 so that the phase of the eccentric cam groove 634 with respect to the drum 61 changes.

By rotating the cam disc 635 in either direction (see arrows of FIG. 6) by the electric motor 638, the phase of the eccentric cam groove 634 is adjusted.

According to the vertically moving cam mechanisms 630 and the phase adjusting mechanism 631, the claw members 607 for pressing the part of the sheet W between the crotch parts against the peripheral surface of the drum 61 vertically move according to the rotation of the drum 61. Specifically, the cam followers 633 are engaged with the eccentric cam groove 634 of the cam disc 635 facing the side surface of the drum 61.

Here, a timing at which the claw members 607 press the part of the sheet W between the crotch parts against the peripheral surface 61*a* of the drum 61 differs depending on the size of the wearable articles P (L size, M size, S size, etc.).

Accordingly, the timing at which the claw members 607 press the part of the sheet W between the crotch parts against the peripheral surface 61*a* of the drum 61 can be adjusted by rotating the cam disc 635 by a predetermined angle by the phase adjusting mechanism 631 to adjust the phase of the eccentric cam groove 634.

Note that the phase of the eccentric cam groove 634 can be adjusted also when the phase of the eccentric cam groove 634 changes to shift the vertical movement timing of the claw members 607 for a certain reason during the production of wearable articles P of the same size.

Since this eliminates the need for time and labor for replacing the cam disc 635 with another one having a different phase of the eccentric cam groove 634 according to the size of the wearable articles P, the production efficiency of the wearable articles P can be improved. Further, even if the vertical movement timing of the claw members 607 is shifted during production, the phase of the eccentric cam groove 634 can be adjusted without stopping a production line, wherefore the production efficiency of the wearable articles P can be improved also in this respect.

Further, the phase adjusting mechanism 631 includes the cam gear 636 formed on the outer periphery of the cam disc 635, the cam drive gear 637 meshed with the cam gear 636 and the electric motor 638 for drivingly rotating the cam drive gear 637.

In this way, the phase of the eccentric cam groove 634 with respect to the drum 61 can be simply and quickly adjusted by rotating the cam disc 645 by the electric motor 638.

Here, the electric motor 638 is preferably a stepping motor capable of finely adjusting the amount of rotation. Further, it is preferable to adopt a motor with a brake capable of fixing the cam disc 635 at a predetermined rotational position as the electric motor 638, but a braking means may be separately provided.

A method for producing a disposable wearable article using the device for producing a disposable wearable article described above is described with reference to FIG. 7.

This producing method includes a conveying process, an absorber arranging process, an elastic attaching process, a hole forming process, a doubling process, a twisting process and a joining/cutting process.

In the conveying process, the sheet W is continuously conveyed along the line L1.

In the absorber arranging process, the absorbers C are intermittently arranged on the surface of the sheet W.

In the elastic attaching process, the waist elastic F is attached to the surface of the sheet W.

In the hole forming process, the holes H, which will become leg holes, are formed at the positions of the sheet W at the opposite sides of the absorber C.

In the doubling process, the sheet W is doubled together with the absorber C such that the opposite side edges W1, W2 of the sheet W having the absorber C thereon are proximate to or overlapped with each other. Further, in the doubling process, the sheet W is doubled such that the sheet W conveyed in the horizontal orientation is arranged in the vertical orientation.

In the twisting process, the sheet W arranged in the vertical orientation in the doubling process is twisted (returned) into the horizontal orientation.

In the joining/cutting process, after the parts of the doubled sheet W at the opposite sides of the absorber C are joined, these joined parts are cut.

Note that the specific embodiment described above mainly includes inventions having the following configurations.

Specifically, the present invention provides a device for producing a disposable wearable article, the device including a doubling unit provided in a line for continuously conveying a sheet and configured to double the sheet together with an absorber such that opposite side edges of the sheet having the absorber arranged thereon are proximate to or overlapped with each other and a joining/cutting unit provided in the line and configured to join parts of the doubled sheet at opposite sides of a crotch part having the absorber arranged thereon and then cut the joined parts, the joining/cutting unit including a drum having a peripheral surface and rotatable with the doubled sheet placed on the peripheral surface, at least one joining mechanism configured to join the parts of the doubled sheet at the opposite sides of the crotch part between the joining mechanism and the drum, a cutting mechanism arranged downstream of the joining mechanism in a rotating direction of the drum and configured to cut the parts of the sheet joined by the joining mechanism between the cutting mechanism and the drum, a claw member mounted on the drum to be vertically movable with respect to the peripheral surface of the drum, and a vertically moving cam mechanism configured to move the claw member downward to press a part of the sheet between the crotch parts against the peripheral surface of the drum on a side upstream of the joining mechanism in the rotating direction of the drum and move the claw member upward to release the pressing on a side downstream of the cutting mechanism in the rotating direction of the drum, the vertically moving cam mechanism including a cam disc having an eccentric cam groove, facing a side surface of the drum and coaxially arranged with the drum and a cam follower provided on the claw member and configured to be engaged with the eccentric cam groove so that the claw member vertically moves according to the rotation of the drum, the joining/cutting unit further including a phase adjusting mechanism capable of adjusting a phase of the eccentric cam groove with respect to the drum.

The claw member configured to press the part of the sheet between the crotch parts against the peripheral surface of the drum vertically moves according to the rotation of the drum. Specifically, the cam follower provided on the claw member is engaged with the eccentric cam groove of the cam disc facing the side surface of the drum.

Here, a timing at which the claw member presses the part of the sheet between the crotch parts against the peripheral surface of the drum differs depending on the size of wearable articles (L size, M size, S size, etc.).

Accordingly, the timing at which the claw member presses the part of the sheet between the crotch parts against the peripheral surface of the drum can be adjusted by adjusting the phase of the eccentric cam groove with respect to the drum by the phase adjusting mechanism.

Note that the phase of the eccentric cam groove can be adjusted also when the phase of the eccentric cam groove changes to shift the vertical movement timing of the claw member for a certain reason during the production of wearable articles of the same size.

Since this eliminates the need for time and labor for replacing the cam disc with another one having a different phase of the eccentric cam groove according to the size of the wearable articles, the production efficiency of the wearable articles can be improved. Further, even if the vertical movement timing of the claw member is shifted during production, the phase of the eccentric cam groove can be adjusted without stopping a production line, wherefore the production efficiency of the wearable articles P can be improved also in this respect.

In the above device for producing a disposable wearable article, the phase adjusting mechanism preferably includes a cam gear formed on an outer periphery of the cam disc, a cam drive gear meshed with the cam gear and an electric motor configured to drivingly rotate the cam drive gear so that the phase of the eccentric cam groove with respect to the drum changes.

According to this configuration, the phase of the eccentric cam groove with respect to the drum can be simply and quickly adjusted by rotating the cam disc by the electric motor.

Here, in the case of applying the mechanism described in patent literature 2 to the device shown in FIG. 7, the part of the sheet W between the crotch parts can be pressed against the peripheral surface of the drum 61 by pressing claws and the like with the lower surface of the doubled sheet W placed on the peripheral surface of the drum 61. This can suppress the lift of the sheet W from the peripheral surface of the drum 61 due to an inertial force associated with the rotation of the drum 61.

However, the crotch part of the sheet W including the absorber C is much thicker than a waist part including no absorber C and the doubled absorber C tries to open itself due to the elasticity thereof. Thus, it is not easy to carry in the crotch part to the peripheral surface of the drum 61 in a proper posture extending along the peripheral surface. In addition, the crotch part is easily lifted up from the peripheral surface of the drum 61 due to the inertial force associated with the rotation of the drum 61. If the crotch part is lifted up from the peripheral surface of the drum 61 as just described, the crotch part is more likely to interfere with the succeeding joining mechanism and cutting mechanism, thereby causing problems such as the damage of the crotch part.

Accordingly, in the above device for producing a disposable wearable article, the joining/cutting unit preferably further includes a pressing mechanism provided on a carry-in side of the doubled sheet with respect to the drum and configured to press the crotch part against the peripheral surface of the drum when the doubled sheet is carried in to the peripheral surface.

According to this configuration, the crotch part can be pressed against the peripheral surface of the drum when the doubled sheet is carried in to the peripheral surface. Thus, the crotch part can be carried in to the peripheral surface of the drum in a proper posture extending along the peripheral surface of the drum.

As a result, the crotch part of the doubled sheet and the part thereof between the crotch parts are held at proper positions on the drum peripheral surface and cut at desired positions.

The crotch part carried in to the peripheral surface of the drum can be pressed against the drum peripheral surface using an arbitrary means. For example, the peripheral surface of the drum is formed with an air suction hole for sucking and holding the crotch part of the doubled sheet and the pressing mechanism can be configured to press the crotch part against the air suction hole.

According to this configuration, the crotch part can be held on the peripheral surface of the drum against an inertial force associated with the rotation of the drum by sucking air through the air suction hole. Thus, the lift of the crotch part from the peripheral surface of the drum can be suppressed.

As a result, the interference of the crotch part with the succeeding joining mechanism and cutting mechanism can be suppressed, thereby being able to prevent the damage of the crotch part and the like.

Further, since the crotch part can be continuously sucked and held also after the wearable article is separated from the sheet by the cutting mechanism, the wearable article can be fed to the next process by releasing the suction holding at a suitable rotational position of the drum.

In the above device for producing a disposable wearable article, the pressing mechanism preferably further includes a rotational shaft configured to be rotated in synchronization with the drum and a pressing cam projecting radially outwardly of the rotational shaft from the rotational shaft and configured to press the crotch part against the peripheral surface of the drum.

According to this configuration, the pressing cam is provided on the rotational shaft configured to rotate in synchronization with the drum. Thus, by matching a timing at which the pressing cam and the peripheral surface of the drum approach each other with a conveying timing of the crotch part, the crotch part can be pressed against the peripheral surface of the drum in a pinpoint manner. Therefore, the crotch part can be reliably pressed against the peripheral surface while adopting a simple structure.

Here, in the case of using a belt for synchronizing the joining mechanism and the cutting mechanism respectively with the drum 61 in the joining/cutting unit 60 shown in FIG. 7, there will be operational shifts between the joining mechanism, the cutting mechanism and the drum if the belt slips or is stretched. As a result, the joining position and the cutting position of the sheet W may vary. Particularly, in the case of successively heat-sealing the same part of the sheet W a plurality of times, e.g. three times, three joining positions vary to case problems such as an adhesion failure.

Accordingly, in the above device for producing a disposable wearable article, each of the at least one joining mechanism includes a joining rotary shaft and a seal member mounted on the joining rotary shaft to be rotatable about the joining rotary shaft and configured to join parts of the sheet, the cutting mechanism includes a cutting rotary shaft and a cutter mounted on the cutting rotary shaft to be rotatable about the cutting rotary shaft and configured to cut the joined parts, the joining/cutting unit further includes a synchronously rotating mechanism configured to rotate the seal member, the cutter, and the drum in synchronization with each other, and the synchronously rotating mechanism includes a drum gear provided on the drum, a joining gear provided on the joining rotary shaft and meshed with the drum gear and a cutting gear provided on the cutting rotary shaft and meshed with the drum gear.

According to this configuration, the joining gear and the cutting gear respectively directly meshed with the drum gear of the drum are provided and the joining mechanism and the cutting mechanism are rotated in synchronization with the drum by these meshes.

Note that, in the case of using a belt for synchronizing the joining rotary shaft of the seal member and the cutting rotary shaft of the cutter with the drum, there will be operational shifts between the joining rotary shaft, the cutting rotary shaft and the drum if the belt slips or is stretched. As a result, the joining position and the cutting position of the sheet may vary.

In contrast, in this configuration, the seal member and the cutter can be rotated perfectly synchronized with the rotation of the drum by respectively directly meshing with the joining gear and the cutting gear with the drum gear. Thus, variations of the joining position and the cutting position of the sheet W can be prevented. As a result, the quality of wearable articles can be improved.

In the above device for producing a disposable wearable article, the joining/cutting unit preferably includes a plurality of the joining mechanisms arranged side by side in the rotating direction of the drum and configured to successively heat-seal the same part of the sheet a plurality of times.

Even in the case of successively heat-sealing a plurality of times, e.g. three times in this way, a trouble of varying three joining positions of the sheet can be suppressed. As a result, the sheet can be reliably joined and the quality of wearable articles can be further improved.

Further, the present invention provides a method for producing a disposable wearable article using the above device for producing a disposable wearable article, the method including a conveying process of continuously conveying a sheet, an absorber arranging process of arranging an absorber on a surface of the sheet, a doubling process of doubling the sheet together with the absorber using the above doubling unit such that opposite side edges of the sheet having the absorber arranged thereon are proximate to or overlapped with each other and a joining/cutting process of joining parts of the doubled sheet at opposite sides of a crotch part having the absorber arranged thereon and then cutting the joined parts using the above joining/cutting unit.

According to the present invention, the joining/cutting process is performed using the above joining/cutting unit. Since this eliminates the need for time and labor for replacing the cam disc with another one having a different phase of the eccentric cam groove according to the size of wearable articles, the production efficiency of the wearable articles can be improved. Further, even if the vertical movement timing of the claw member is shifted during production, the phase of the eccentric cam groove can be adjusted without stopping a production line, wherefore the production efficiency of the wearable articles can be improved also in this respect.

The invention claimed is:

1. A device for producing a disposable wearable article, comprising:
a doubling unit provided in a line for continuously conveying a sheet and configured to double the sheet together with an absorber such that opposite side edges of the sheet having the absorber arranged thereon are proximate to or overlapped with each other; and
a joining/cutting unit provided in the line and configured to join parts of the doubled sheet at opposite sides of a crotch part having the absorber arranged thereon and then cut the joined parts,
the joining/cutting unit including a drum having a peripheral surface and rotatable with the doubled sheet placed on the peripheral surface, at least one joining mechanism configured to join the parts of the doubled sheet at the opposite sides of the crotch part between the joining mechanism and the drum, a cutting mechanism arranged downstream of the joining mechanism in a rotating direction of the drum and configured to cut the parts of the sheet joined by the joining mechanism between the cutting mechanism and the drum, a claw member mounted on the drum to be vertically movable with respect to the peripheral surface of the drum, and a vertically moving cam mechanism configured to move the claw member downward to press a part of the sheet between the crotch parts against the peripheral surface of the drum on a side upstream of the at least one joining mechanism in the rotating direction of the drum and move the claw member upward to release the pressing on a side downstream of the cutting mechanism in the rotating direction of the drum,
the vertically moving cam mechanism including a cam disc having an eccentric cam groove, facing a side surface of the drum and coaxially arranged with the drum and a cam follower provided on the claw member and configured to be engaged with the eccentric cam groove so that the claw member vertically moves according to the rotation of the drum, and
the joining/cutting unit further including a phase adjusting mechanism capable of adjusting a phase of the eccentric cam groove with respect to the drum.

2. A device for producing a disposable wearable article according to claim 1, wherein:
the phase adjusting mechanism includes a cam gear formed on an outer periphery of the cam disc, a cam drive gear meshed with the cam gear and an electric motor configured to drivingly rotate the cam drive gear so that the phase of the eccentric cam groove with respect to the drum changes.

3. A device for producing a disposable wearable article according to claim 1, wherein:
the joining/cutting unit further includes a pressing mechanism provided on a carry-in side of the doubled sheet with respect to the drum and configured to press the crotch part against the peripheral surface of the drum when the doubled sheet is carried in to the peripheral surface.

4. A device for producing a disposable wearable article according to claim 3, wherein:
the peripheral surface of the drum is formed with an air suction hole for sucking and holding the crotch part of the doubled sheet; and
the pressing mechanism is configured to press the crotch part against the air suction hole.

5. A device for producing a disposable wearable article according to claim 3 wherein:
the pressing mechanism further includes a rotational shaft configured to be rotated in synchronization with the drum and a pressing cam projecting radially outwardly of the rotational shaft from the rotational shaft and configured to press the crotch part against the peripheral surface of the drum.

6. A device for producing a disposable wearable article according to claim 1, wherein:
each of the at least one joining mechanism includes a joining rotary shaft and a seal member mounted on the joining rotary shaft to be rotatable about the joining rotary shaft and configured to join parts of the sheet;
the cutting mechanism includes a cutting rotary shaft and a cutter mounted on the cutting rotary shaft to be rotatable about the cutting rotary shaft and configured to cut the joined parts;
the joining/cutting unit further includes a synchronously rotating mechanism configured to rotate the seal member, the cutter, and the drum in synchronization with each other; and
the synchronously rotating mechanism includes a drum gear provided on the drum, a joining gear provided on the joining rotary shaft and meshed with the drum gear and a cutting gear provided on the cutting rotary shaft and meshed with the drum gear.

7. A device for producing a disposable wearable article according to claim 6, wherein:
the joining/cutting unit includes a plurality of the joining mechanisms arranged side by side in the rotating direction of the drum and configured to successively heat-seal the same part of the sheet a plurality of times.

8. A method for producing a disposable wearable article using a device for producing a disposable wearable article according to claim 1, comprising:
a conveying process of continuously conveying a sheet;
an absorber arranging process of arranging an absorber on a surface of the sheet;
a doubling process of doubling the sheet together with the absorber using the doubling unit such that opposite side edges of the sheet having the absorber arranged thereon are proximate to or overlapped with each other; and
a joining/cutting process of joining parts of the doubled sheet at opposite sides of a crotch part having the absorber arranged thereon and then cutting the joined parts using the joining/cutting unit.

* * * * *